(12) United States Patent
Erman et al.

(10) Patent No.: US 7,968,744 B2
(45) Date of Patent: Jun. 28, 2011

(54) PHYSIOLOGICAL COOLANTS BASED ON LACTOYL ESTERS OF MENTHYL LACTATE

(75) Inventors: Mark B. Erman, Atlantic Beach, FL (US); Patrick J. Whelan, Fernandina Beach, FL (US); Joe W. Snow, Kingsland, GA (US)

(73) Assignee: Renessenz, LLC, Jacksonville, FL (US)

( * ) Notice: Subject to any disclaimer, the term of this patent is extended or adjusted under 35 U.S.C. 154(b) by 0 days.

(21) Appl. No.: 12/806,337

(22) Filed: Aug. 10, 2010

(65) Prior Publication Data

US 2010/0311833 A1 Dec. 9, 2010

Related U.S. Application Data

(62) Division of application No. 11/974,575, filed on Oct. 15, 2007, now Pat. No. 7,803,963.

(51) Int. Cl.
*C07C 69/66* (2006.01)
(52) U.S. Cl. ...................................... 560/188
(58) Field of Classification Search .................. None
See application file for complete search history.

(56) References Cited

U.S. PATENT DOCUMENTS

| 4,136,163 A | 1/1979 | Watson et al. |
| 4,150,052 A | 4/1979 | Watson et al. |
| 4,153,679 A | 5/1979 | Rowsell et al. |
| 5,698,181 A | 12/1997 | Luo |
| 6,048,549 A | 4/2000 | Nitikhunkasem et al. |
| 6,379,652 B1 | 4/2002 | Liu et al. |
| 7,173,146 B1 * | 2/2007 | Erman et al. ............ 560/188 |
| 7,189,760 B2 | 3/2007 | Erman et al. |
| 2004/0018954 A1 | 1/2004 | Su et al. |
| 2004/0082654 A1 | 4/2004 | Pesce et al. |

FOREIGN PATENT DOCUMENTS

DE 2608226 9/1977

OTHER PUBLICATIONS

Smith et al., "GRAS Flavoring Substances 20", *Food Technol.* 55 (2001) 34, pp. 44 and 53.
Watson et al., "New Compounds With the Menthol Cooling Effect" *J. Soc. Cosmet. Chem.* 29 (1978) 185.
Erman et al., "New Developments in Physiological Cooling Agents: Examining the rapid devlopment in the chemistry and use of cooling agents," *Perfumer & Flavorist*, vol. 32, (2007), 20-35.

* cited by examiner

*Primary Examiner* — Karl J Puttlitz
(74) *Attorney, Agent, or Firm* — Novak Druce + Quigg LLP

(57) ABSTRACT

A method of imparting a physiological cooling effect to a consumer product is disclosed. The method comprises formulating into the consumer product a composition comprising at least one lactoyl ester of menthyl lactate. Also disclosed is a method of providing physiological cooling by contacting skin or mucous membranes with the lactoyl ester compositions. Coolants comprising the lactoyl esters and additional coolants are also disclosed. The lactoyl esters are conveniently prepared from menthol and lactic acid.

11 Claims, No Drawings

PHYSIOLOGICAL COOLANTS BASED ON LACTOYL ESTERS OF MENTHYL LACTATE

CROSS-REFERENCE TO RELATED APPLICATION

This is a division of application. Ser. No. 11/974,575, filed Oct. 15, 2007 now U.S. Pat. No. 7,803,963.

FIELD OF THE INVENTION

The invention relates to physiological coolants based on lactoyl esters of menthyl lactate and their use in consumer products.

BACKGROUND OF THE INVENTION

Physiological coolants impart a cooling and/or refreshing sensation to skin or mucous membranes and thereby improve the properties of foods, confections, cosmetics, medications, and other consumer goods.

l-Menthol is a strong, natural physiological coolant. However, in many compositions l-menthol is undesirable due to its pungent minty odor and bitter taste. At least eleven synthetic replacements for l-menthol are now commercially available and have been approved by FEMA as "GRAS" (generally recognized as safe) compositions. Examples include N-ethyl-3-p-menthane carboxamide ("WS-3," see U.S. Pat. No. 4,150,052), 2-isopropyl-N,2,3-trimethyl butanamide ("WS-23," U.S. Pat. No. 4,153,679), menthyl lactate (DE 2,608, 226), monomenthyl glutarate (Food Technol. 55 (2001) 34), and N-ethoxycarbonylmethyl-3-p-menthane carboxamide ("WS-5," U.S. Pat. No. 7,189,760). Commercial coolants incorporate many different functional groups, including carboxamides, esters, ethers, alcohols, diols, and heterocycles. Each has its own character, including not only cooling strength and threshold of perception, but also longevity of cooling action, taste and aftertaste, compatibility and/or synergy with other ingredients of the composition, physical state under ambient conditions, solubility, and other attributes.

Menthyl lactate (ML), normally prepared by direct esterification of lactic acid with menthol, is a widely used coolant for flavors, oral care, and cosmetics. The most common ML isomer, 1, derives from l-menthol and L(+)-lactic acid:

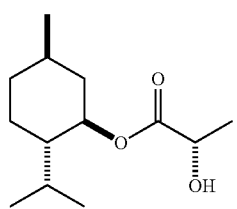

1

We recently reported (see U.S. Pat. No. 7,173,146) that the reaction of lactic acid and menthol produces not only ML but also significant amounts of higher lactoyl esters of ML, including menthyl lactoyl lactate MLL) and menthyl lactoyl lactoyl lactate (MLLL):

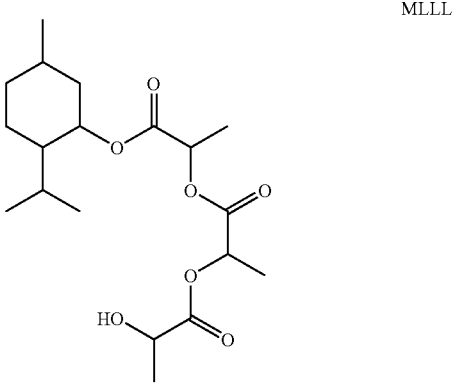

Although the lactoyl esters can comprise 25% or more of a direct esterification mixture, earlier processes had discarded them in the distillation process used to isolate ML. We discovered that controlled hydrolysis with aqueous base could selectively convert the lactoyl esters back to ML without also hydrolyzing ML, thereby maximizing the overall yield of ML. Cooling properties of the lactoyl esters were not investigated and went unnoticed.

Interest in new coolants is accelerating, fueled by expanding applications, a global consumer base, and demand for an array of goods with diverse properties such as taste, odor, freshness, and overall perception. Cost often limits coolant choices in applications such as chewing gum, for which significant concentrations of the coolant are needed. Regulatory factors can also be important. For instance, carboxamides are not currently acceptable food additives in Japan.

In sum, new coolants are needed, particularly ones that are made from inexpensive starting materials and are free of nitrogen-containing groups such as amides. Unfortunately, there is no way to easily predict the cooling properties of a compound from its structure, though some (see, e.g., J. Soc. Cosmet. Chem. 29 (1978) 185) have tried. Finding useful, inexpensive coolants remains mostly a matter of serendipity.

SUMMARY OF THE INVENTION

In one aspect, the invention is a method of imparting a physiological cooling effect to a consumer product. The method comprises formulating into the consumer product a composition comprising at least one lactoyl ester of menthyl lactate. In another aspect, the physiological cooling effect is provided to mammalian skin or mucous membranes by contacting them with the lactoyl ester composition. The invention includes consumer products that comprise at is least one lactoyl ester of menthyl lactate. Also included are liquid cooling compositions that comprise the lactoyl ester and an additional coolant such as WS-3, WS-23, monomenthyl glutarate, or WS-5.

We surprisingly found that lactoyl esters of menthyl lactate possess physiological cooling activity and are comparable to or stronger than monomenthyl glutarate, a commercial coolant. The lactoyl esters are easy to make from inexpensive lactic acid, and they are valuable components of liquid cooling compositions known as "coolant cocktails."

DETAILED DESCRIPTION OF THE INVENTION

Lactoyl esters of menthyl lactate are conveniently produced by reacting menthol with two or more molar equivalents of lactic acid.

Menthol suitable for use in the invention can have any desired stereochemistry. With three chiral centers, menthol has eight possible stereoisomers. A menthol sample might have several different stereoisomers present. Examples include l-menthol, d-menthol, dl-menthol (i.e., a racemic mixture of l-menthol and d-menthol), isomers of neomenthol, isomenthol, and neoisomenthol, and mixtures thereof.

l-Menthol, d-menthol, dl-menthol, and other isomers are all commercially available. Because it provides lactoyl esters of ML having excellent physiological cooling properties, l-menthol (2) is particularly preferred.

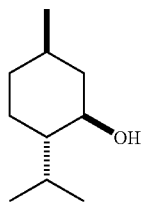

2

Lactic acid reacts with menthol to make lactoyl esters of ML. With one chiral center, lactic acid has two possible stereoisomers, L-(+)-lactic acid and D-(−)-lactic acid. Lactic acid is commonly supplied as a concentrated solution in water (e.g., 85+ wt. % lactic acid). An example is HS-88 solution, a product of Purac, which contains about 88 wt. % of lactic acid in water. Suitable lactic acid for use herein includes L-(+)-lactic acid, D-(−)-lactic acid, the racemic mixture (i.e., DL-lactic acid), and mixtures thereof. Because it provides lactoyl esters of ML having excellent physiological cooling properties, L-(+)-lactic acid (3) is particularly preferred.

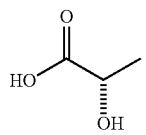

3

Esterification of lactic acid with menthol generally produces a mixture comprising menthyl lactate and one or more lactoyl esters of menthyl lactate. Simply heating menthol and lactic acid together (usually in the presence of a solvent such as heptane, toluene, or the like to assist in removing water formed as a result of esterification) generates lactoyl esters of ML, including MLL, MLLL, and traces of even higher esters.

How the lactoyl esters form is not critical. The mechanism may involve successive formation of ML, MLL, MLLL, and so on, as additional lactic acid condenses with the lower ester. Of course, other mechanisms are possible, including initial formation of lactic acid oligomers followed by condensation with menthol, a combination of the two mechanisms described above, or some other pathway.

In one aspect of the invention, the lactoyl esters are made by reacting l-menthol with an excess, preferably at least two molar equivalents, of optically pure L-(+)-lactic acid to provide l-menthyl L-lactoyl-L-lactate (4a):

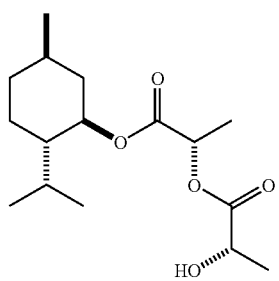

4a

In another aspect, l-menthol reacts with excess DL-lactic acid, a racemic mixture, to provide a mixture of four MLL stereoisomers, i.e., l-menthyl L-lactoyl-L-lactate (4a), l-menthyl L-lactoyl-D-lactate (4b), l-menthyl D-lactoyl-L-lactate (4c), and l-menthyl D-lactoyl-D-lactate (4d):

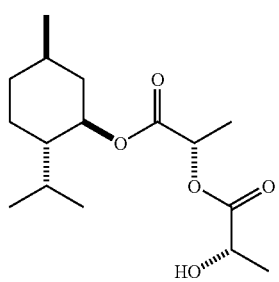

4a

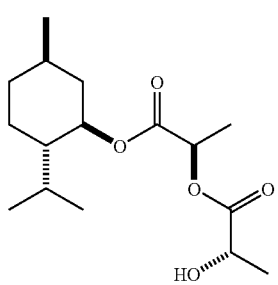

4b

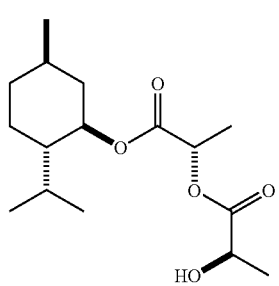

4c

-continued

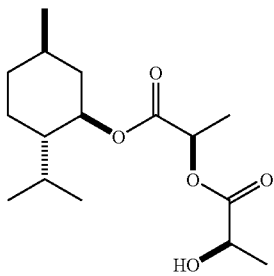

4d

The direct esterification process for making lactoyl esters of ML usually generates a reaction mixture that contains unreacted menthol and/or cyclic dimers of lactic acid ("lactides") in addition to ML and the desired lactoyl esters. As noted earlier, water of reaction is preferably removed to promote esterification; a hydrocarbon solvent and a Barrett or Dean-Stark trap are advantageously used.

The esterification is performed at any convenient temperature and under conditions effective to maximize production of lactoyl esters of ML. Generally, the esterification proceeds over a range of temperatures that depend on whether a solvent is included, and if so, the identity and boiling point of the solvent. The temperature generally increases as the reaction approaches completion. Often, the esterification proceeds at or near the reflux temperature of the reaction mixture. When heptane is the solvent, for example, the esterification proceeds within the range of about 80° C. to about 130° C.

Preferably, no catalyst is used to promote the esterification reaction. However, a catalyst can be included. Suitable esterification catalysts are typically acids. Suitable catalysts include, for example, sulfuric acid, acidic ion-exchange resins, organic sulfonic acids (e.g., p-toluenesulfonic acid), alkali metal bisulfates, or the like, and mixtures thereof.

The esterified product containing lactoyl esters of ML can be purified, if desired, by any suitable means, including distillation, crystallization, or the like, or a combination of techniques. As shown below in Synthetic Example 1, high-purity MLL can be isolated by vacuum distillation followed by crystallization. Sensory evaluation (Table 1) indicates that pure MLL has a clean, smooth cooling effect and a strength that is intermediate between that of l-menthyl lactate and monomenthyl glutarate.

Isolating pure MLL can be costly, so the product mixtures containing MLL are preferably used for coolant applications after performing a simple workup, usually aqueous extraction, to remove unreacted lactic acid. The resulting product mixture usually contains menthol and menthyl lactate in addition to the desired lactoyl esters, and it may include other components such as higher lactoyl esters (e.g., MLLL) and lactides. Because the principal components of the mixture are active coolants, however, there is usually no need to isolate pure MLL. Synthetic Examples 3 and 5 below illustrate how to prepare liquid mixtures comprising menthyl lactate, MLL, and MLLL. Sensory evaluation of such liquid mixtures confirms that they have a clean, smooth cooling effect and a strength generally comparable to that of monomenthyl glutarate.

In one aspect, the invention is a method of imparting a physiological cooling effect to a consumer product. The method comprises formulating into the consumer product a composition comprising at least one lactoyl ester of menthyl lactate. Preferably, the lactoyl ester is menthyl lactoyl lactate (MLL).

The lactoyl ester-containing composition is often a liquid mixture that may contain one or more other physiological coolants. Preferably, the additional coolant is selected from substituted cyclonexanols and their esters, carboxamides, menthone ketals, menthoxypropanediols, and mixtures thereof. Particular examples of additional coolants include menthol, isopulegol, menthyl lactate, N-ethyl-3-p-menthane carboxamide (WS-3), 2-isopropyl-N,2,3-trimethyl butanamide (WS-23), N-ethoxy-carbonylmethyl-3-p-menthane carboxamide (WS-5), monomenthyl glutarate, monomenthyl succinate, and mixtures thereof.

Preferably, the consumer product is a food, confection, chewing gum, beverage, cosmetic, toothpaste, mouthwash, shampoo, toiletry, lotion, medication, pharmaceutical, or the like. Other and more particular suitable consumer product applications for physiological coolants have been described (see, e.g., U.S. Pat. Nos. 4,136,163 and 7,189,760). The invention includes consumer products comprising at least one lactoyl ester of menthyl lactate.

In another aspect, the invention provides the physiological cooling effect by contacting mammalian skin or mucous membranes with a composition comprising at least one lactoyl ester of menthyl lactate. Again, the lactoyl ester composition may be a liquid mixture containing one or more other physiological coolants as described hereinabove. The composition can be applied using any suitable method known to those skilled in the art and obviously depends on the particular application. Skin contact is the preferred route for lotions, cosmetics, shampoos, and topical medications, while contacting mucous membranes applies to foods, confections, chewing gum, beverages, mouthwashes, and the like.

The compositions comprising at least one lactoyl ester of menthyl lactate are preferably used in an amount effective to provide a physiological cooling effect when formulated into a consumer product or contacted with mammalian skin or mucous membranes. The actual amount needed will depend on many factors, including the particular end-use application, desired cooling profile, identity and amounts of any other coolants in the composition, and other considerations. Normally, the amount needed is determined empirically by the skilled person. Generally, the amount used will be within the range of 0.1 ppm to 5 wt. % (50,000 ppm), preferably from 5 ppm to 1 wt. %. In a topical application such as a lotion or hand cream, for example, the amount of menthyl lactate lactoyl ester composition required will typically range from 100 ppm to 5 wt. %. Low concentrations (0.1 ppm to 100 ppm) should be more suitable for beverages, while intermediate levels (10 ppm to. 5,000 ppm) are normally desirable for a toothpaste, chewing gum, candy, or mouthwash.

The invention includes liquid cooling compositions. The compositions comprise at least one lactoyl ester of menthyl lactate and one or more coolants selected from the group consisting of WS-3, WS-23, WS-5, monomenthyl glutarate, monomenthyl succinate, and mixtures thereof. Compositions that are stable liquids under ambient conditions are usually far easier to formulate homogeneously into the desired end-use application than solid coolants, and they often avoid or reduce the need for solvents or other diluents.

Menthyl lactoyl lactate is a valuable component of liquid coolant mixtures, including "coolant cocktails." Synthetic Examples 3 and 5 below illustrate the preparation of liquid mixtures comprising menthyl lactoyl lactate and other related coolants such as menthol and menthyl lactate. The liquid mixtures can be used "as is," or they can be combined with other valuable coolants such as WS-3, WS-5, WS-23, and monomenthyl glutarate to provide excellent coolant cocktails (see Table 2, Examples 6-11). Using the liquid mixture comprising menthyl lactoyl lactate in combination with such commercial coolants may reduce the cost, enhance the cooling profile, or make formulating the coolant mixture into the end-use application easier. When the liquid mixtures are used in coolant cocktails, they preferably comprise at least 35 wt. %, more preferably at least 50 wt. %, and most preferably at least 80 wt. % of the coolant cocktail.

The following examples merely illustrate the invention. Those skilled in the art will recognize many variations that are within the spirit of the invention and scope of the claims.

SYNTHETIC EXAMPLE 1

Preparation of l-Menthyl L-Lactoyl-L-Lactate

A three-neck flask equipped with a Barrett trap, reflux condenser, thermocouple, heating mantle, and magnetic stirrer is charged with l-menthol (1000 g), L-(+)-lactic acid (2000 g of grade HS-88 from Purac, 88% lactic acid in water), and heptane (500 g). The stirred mixture is brought to reflux and water is periodically drained from the trap as it forms. The temperature of the mixture increases gradually to 123° C. after 29 h and after 580 mL of aqueous phase has been removed. The mixture is cooled to ambient temperature and analyzed by gas-liquid chromatography (GC). It contains: 7.3% of unreacted menthol, 50.5% of l-menthyl L-lactate (ML), 3.3% of lactide (cyclic dimer of lactic acid), 35.2% of l-menthyl L-lactoyl-L-lactate (MLL), and 2.5% of l-menthyl L-lactoyl-L-lactoyl-L-lactate (MLLL).

A portion (1094 g) of this mixture is diluted with water (1317 g) and heptane (378 g), and excess lactic acid is neutralized to pH 7.1 with aqueous sodium hydroxide (167 g of 50% NaOH). The layers are separated. The organic layer is washed with 1% lactic acid (500 g) and filtered through a pad of anhydrous sodium sulfate. Heptane is stripped by rotary evaporation, and the residue is vacuum distilled. Fractions boiling higher than 120° C. at ~3 mm are combined and subjected to multiple crystallizations from heptane until the purity exceeds 99% by gas chromatography (GC). Melting point: 59° C.

$^1$H NMR(CDCl$_3$, 300 Mhz), δ ppm: 0.73 d (3H, methyl at cyclohexane group); 0.86 br. d (6H, methyls in isopropyl group); 1.45 d and 1.47 d (3H and 3H, methyls in two lactic residues); 2.81 br. d (1H, OH); 4.32 m (1H, CH-0 at cyclohexane); 4.68 m (1H, CH-0 in a terminal lactic residue); and 5.09 q (1H, CH-0 in a middle lactic residue). Other CH signals from the menthyl group appear as multiplets within the range of 0.8-2.0 ppm.

$^{13}$H NMR (CDCl$_3$, 75 MHz), δ ppm: 16.30 (CH$_3$), 16.82 (CH$_3$), 20.49 (CH$_3$), 20.55 (CH$_3$), 21.89 (CH$_3$), 23.51 (CH$_2$), 26.28 (CH), 31.31 (CH), 34.11 (CH$_2$), 40.51 (CH$_2$), 46.95 (CH), 66.62 (CH—O), 69.53 (CH—O), 75.63 (CH—O), 169.74 (C=O), 175.04 (C=O).

SYNTHETIC EXAMPLE 2

Preparation of l-Menthyl L-Lactoyl-L-Lactate

The procedure of Example 1 is repeated, except that the amount of l-menthol is reduced to 500 g. After 54 hours of reflux and water removal (547 g), the reaction mixture is washed with water and neutralized to pH 6.4. By GC analysis, the mixture contains: 2.6% of unreacted l-menthol, 2.6% of lactide, 45.9% of ML, 40.6% of MLL, and 6.6% of MLLL. MLL is isolated and purified as described in Example 1.

SYNTHETIC EXAMPLE 3

Preparation of a Liquid Mixture Comprising ML, l-Menthyl L-Lactoyl-L-Lactate, and MLLL The procedure of Example 1 is generally followed. After the usual reflux and water removal, the mixture is cooled, and a portion (785 g) is washed with water (1900 g) to remove unreacted lactic acid. The organic phase (719 g) is neutralized with 4% aqueous NaOH solution (about 340 g) to pH 5.8. The layers are separated, and the organic layer is washed with water (1200 g) for 1 h, dried (anhydrous Na$_2$SO$_4$), and stripped. To remove traces of heptane, the mixture is sparged with nitrogen. The resulting liquid homogeneous mixture (470 g) contains (GC): 37.0% of l-menthyl L-lactoyl-L-lactate, 49.0% of ML, 6.0% of l-menthol, 4.1% of MLLL, and 2.6% of lactide.

SYNTHETIC EXAMPLE 4

Preparation of MLL from l-Menthol and Dl-Lactic Acid

The procedure of Example 2 is followed except that DL-lactic acid is instead of L-(+)-lactic acid. After 49 h of reflux and water removal (547 g), the reaction mixture is washed with water and neutralized to pH 6.4. The mixture contains: 3.0% of unreacted l-menthol, 0.7% of lactide, 22.2% of l-menthyl L-lactate, 22.7% of l-menthyl D-lactate; a total of 42.0% of the four isomers of l-menthyl lactoyl lactate, including l-menthyl L-lactoyl-L-lactate 4a, l-menthyl L-lactoyl-D-lactate 4b, l-menthyl D-lactoyl-L-lactate 4c, and l-menthyl D-lactoyl-D-lactate 4d in about equal concentrations (10.5±1.0%). The balance (about 9%) is a plurality of MLLL oligomers. The mixture is distilled, and a fraction containing predominantly the four isomers of l-menthyl lactoyl lactate is collected as a viscous liquid with a boiling range from about 105° C. at 0.5 mm to about 145° C. at 0.5 mm.

SYNTHETIC EXAMPLE 5

Preparation of a Liquid Mixture Comprising l-Menthol, l-Menthyl-D,L-Lactates, and MLL Isomers The procedure of Example 1 is generally followed except that 500 g of l-menthol and DL-lactic acid (minimum 85% in water; Sigma-Aldrich, 2000 g) are used. After the usual reflux and water removal, the mixture is cooled, and the mixture is washed with water remove unreacted DL-lactic acid and the organic phase is neutralized with 4% aqueous NaOH solution to pH 6. The layers are separated, and the organic layer is washed with water, dried, and stripped. To remove traces of heptane, the mixture is sparged with nitrogen. The resulting liquid homogeneous mixture (1062 g) contains (GC): 3.0% of l-menthol; 22.3% of l-menthyl L-lactate; 22.9% of l-menthyl D-lactate; a total of about 44% of MLL isomers, including l-menthyl L-lactoyl-L-lactate 4a, l-menthyl L-lactoyl-D-lactate 4b, l-menthyl D-lactoyl-L-lactate 4c, and l-menthyl D-lactoyl-D-lactate 4d in about equal concentrations (11±1%). The balance (about 9%) is a plurality of MLLL oligomers.

EXAMPLES 6-10

Sensory Properties of MLL and Liquid Mixtures Containing MLL

The sensory properties of crystalline MLL and liquid products that contain MLL (from Examples 1-5, above) are evaluated by a panel of three flavorists. The standard method involves holding an aqueous solution containing 20 ppm of coolant in the mouth for 30 seconds, then spitting it out and observing and quantifying the cooling effect when compared with a set of reference standards. Based on their cooling strength, the samples are scored on a scale of 1 to 10, with 10 being the strongest. Samples used as reference standards are to monomenthyl glutarate (3.5 on this scale), l-menthyl lactate (4.5) and N-ethyl-3-p-menthane carboxamide, i.e., WS-3 (10). Results appear in Table 1.

TABLE 1

Sensory Evaluation Results

| Ex. # | Source | Product tested | Score | Perception |
|---|---|---|---|---|
| 6 | Synth. Ex. 1 | l-menthyl L-lactoyl-L-lactate crystals (99%) | 4.0 | clean, smooth |
| 7 | Synth. Ex. 2 | l-menthyl L-lactoyl-L-lactate crystals (99%) | 4.0 | clean, smooth |
| 8 | Synth. Ex. 3 | Liquid mixture from L-(+)-lactic acid (%): ML (49), MLL (37), l-menthol (6) | 4.0 | clean, smooth |
| 9 | Synth. Ex. 4 | Liquid mixture of four MLL isomers from DL-lactic acid, isolated by distillation | 3.0 | clean, smooth |
| 10 | Synth. Ex. 5 | Liquid mixture from DL-lactic acid (%): ML (45), MLL isomers (42), l-menthol (3) | 3.5 | clean, smooth |

EXAMPLES 11-18

Cocktails Containing MLL and Additional Coolants

Several coolant "cocktails," i.e., liquid coolant-mixtures, are prepared, and their sensory properties are evaluated as in Example 6. The compositions and results appear in Table 2.

TABLE 2

Evaluation Results for MLL-Containing Coolants

| Ex. # | Liquid mixture (wt. %) | Other coolant (wt. %) | Score |
|---|---|---|---|
| 11 | Synth. Ex. 3 (90) | WS-3 (10) | 5.0 |
| 12 | Synth. Ex. 3 (90) | WS-23 (10) | 4.5 |
| 13 | Synth. Ex. 3 (90) | WS-5 (10) | 5.5 |
| 14 | Synth. Ex. 3 (90) | monomenthyl glutarate (10) | 4.0 |
| 15 | Synth. Ex. 5 (90) | WS-3 (10) | 4.5 |
| 16 | Synth. Ex. 5 (90) | WS-23 (10) | 4.0 |
| 17 | Synth. Ex. 5 (90) | WS-5 (10) | 5.0 |
| 18 | Synth. Ex. 5 (90) | monomenthyl glutarate (10) | 3.5 |

The preceding examples are meant only as illustrations. The following claims define the invention.

We claim:

1. A consumer product selected from the group consisting of foods, beverages, toiletries, lotions, medications, and pharmaceuticals, said consumer product comprising from 0.1 ppm to 5 wt. % of at least one lactoyl ester of menthyl lactate, wherein the liquid mixture further comprises a coolant selected from the group consisting of substituted cyclohexanols and their esters, carboxamides, menthone ketals, and mixtures thereof.

2. The consumer product of claim 1 wherein the food is a confection or chewing gum.

3. The consumer product of claim 1 wherein the toiletry is a cosmetic, toothpaste, mouthwash, shampoo, or lotion.

4. The consumer product of claim 1 wherein the lactoyl ester is menthyl lactoyl lactate (MLL).

5. The consumer product of claim 4 wherein the MLL is prepared by reacting l-menthol and an excess of L-(+)-lactic acid.

6. The consumer product of claim 4 comprising a liquid mixture comprising MLL.

7. The consumer product of claim 1 wherein the liquid mixture comprises a coolant selected from the group consisting of menthol, isopulegol, menthyl lactate, WS-3, WS-23, WS-5, monomenthyl glutarate, monomenthyl succinate, and mixtures thereof.

8. A liquid cooling composition comprising 0.1 ppm to 5 wt. % of at least one lactoyl ester of menthyl lactate; and one or more coolants selected from the group consisting of WS-3, WS-23, WS-5, monomenthyl glutarate, monomenthyl succinate, and mixtures thereof.

9. The composition of claim 8 wherein the lactoyl ester is MLL.

10. The composition of claim 9 wherein the MLL is prepared by reacting l-menthol and an excess of L-(+)-lactic acid.

11. The consumer product of claim 1, wherein the coolant is a menthoxypropanediol.

* * * * *